United States Patent
Sugarman et al.

(10) Patent No.: US 10,085,690 B2
(45) Date of Patent: Oct. 2, 2018

(54) SYSTEM AND METHOD FOR FEEDBACK OF DYNAMICALLY WEIGHTED VALUES

(71) Applicants: Laurence I. Sugarman, Pittsford, NY (US); Brian L. Garrison, Henrietta, NY (US); Stephen Jacobs, Rochester, NY (US)

(72) Inventors: Laurence I. Sugarman, Pittsford, NY (US); Brian L. Garrison, Henrietta, NY (US); Stephen Jacobs, Rochester, NY (US)

(73) Assignee: Rochester Institute of Technology, Rochester, NY (US)

( * ) Notice: Subject to any disclaimer, the term of this patent is extended or adjusted under 35 U.S.C. 154(b) by 0 days.

(21) Appl. No.: 14/740,980

(22) Filed: Jun. 16, 2015

(65) Prior Publication Data

US 2016/0015313 A1 Jan. 21, 2016

Related U.S. Application Data

(60) Provisional application No. 62/012,753, filed on Jun. 16, 2014.

(51) Int. Cl.
*A61B 5/00* (2006.01)
*A61B 5/01* (2006.01)
(Continued)

(52) U.S. Cl.
CPC ............... *A61B 5/486* (2013.01); *A61B 5/01* (2013.01); *A61B 5/02055* (2013.01); *A61B 5/02405* (2013.01); *A61B 5/0531* (2013.01); *A61B 5/0816* (2013.01); *A61B 5/742* (2013.01); *A61B 5/4884* (2013.01); *A61B 5/7271* (2013.01)

(58) Field of Classification Search
CPC ....... A61B 5/486; A61B 5/01; A61B 5/02405; A61B 5/2055; A61B 5/0531; A61B 5/0816; A61B 5/742; A61B 5/4884; A61B 5/7271
See application file for complete search history.

(56) References Cited

U.S. PATENT DOCUMENTS 3,942,516 A * 3/1976 Glynn ................ A61B 5/01 600/545
4,461,301 A * 7/1984 Ochs ................ A61B 5/486 600/301

(Continued)

*Primary Examiner* — Patrick Edouard
*Assistant Examiner* — Eboni Hughes
(74) *Attorney, Agent, or Firm* — Bond, Schoeneck & King, PLLC; Joseph Noto

(57) ABSTRACT

A method and system for monitoring a signal from a function to record a set of values for each signal monitored; determining for each signal monitored the relative value of the signal being monitored over time; identifying each signal exhibiting a relative value representing a change in a pre-identified direction and each signal exhibiting a relative value not representing a change in the pre-identified direction, wherein each signal is aligned in the same direction relative to the pre-identified direction; dynamically weighting at least one signal monitored; displaying the monitored signals as an aggregate including enhancement of each signal exhibiting a change in the pre-identified direction; and causing a desired change in at least one monitored function based upon feedback of the displayed aggregate signals.

16 Claims, 5 Drawing Sheets

(51) Int. Cl.
*A61B 5/0205* (2006.01)
*A61B 5/024* (2006.01)
*A61B 5/053* (2006.01)
*A61B 5/08* (2006.01)

(56) References Cited

U.S. PATENT DOCUMENTS

| | | | | |
|---|---|---|---|---|
| 5,792,047 | A * | 8/1998 | Coggins | A61B 5/486 |
| | | | | 128/905 |
| 7,998,070 | B2 * | 8/2011 | Gentempo, Jr. | A61B 5/015 |
| | | | | 600/301 |
| 9,398,873 | B2 * | 7/2016 | Van Dooren | A61B 5/16 |
| 9,743,848 | B2 * | 8/2017 | Breslow | G06F 19/00 |
| 2004/0116784 | A1 * | 6/2004 | Gavish | A61B 5/0205 |
| | | | | 600/300 |
| 2008/0208016 | A1 * | 8/2008 | Hughes | A61B 5/0533 |
| | | | | 600/301 |
| 2010/0324427 | A1 * | 12/2010 | Devot | A61B 5/0205 |
| | | | | 600/484 |
| 2014/0316230 | A1 * | 10/2014 | Denison | A61B 5/04012 |
| | | | | 600/383 |
| 2015/0031964 | A1 * | 1/2015 | Bly | A61B 5/165 |
| | | | | 600/301 |
| 2015/0217082 | A1 * | 8/2015 | Kang | G16H 50/30 |
| | | | | 600/28 |
| 2016/0234572 | A1 * | 8/2016 | Dixit | G08B 21/0423 |
| 2016/0339300 | A1 * | 11/2016 | Todasco | H04W 4/80 |
| 2017/0071532 | A1 * | 3/2017 | Greco | A61B 5/486 |

* cited by examiner

SYSTEM AND METHOD FOR FEEDBACK OF DYNAMICALLY WEIGHTED VALUES

CROSS REFERENCE

This application claims the benefit of the filing date of U.S. Provisional Patent Application Ser. No. 62/012,753, filed Jun. 16, 2014, which is hereby incorporated by reference in its entirety.

FIELD

This disclosure relates generally to a system and method for monitoring at least one function and more particularly to a system and method for feedback of at least one monitored function as a dynamically weighted value.

BACKGROUND

Standard feedback software can present additional challenges when the monitored function does not always behave in the expected or easily-interpreted ways. For example, in standard biofeedback on a day-to-day basis skin conductance behaves differently. It might change in very small amounts on a cold day, or experience large swings on a humid day. Likewise, participants with developmental differences manifest physiological differences that can reduce their benefit from standard feedback.

Prior technology allows for multiple signals to be displayed at the same time, though typically as disconnected pieces. Signals are also generally displayed in their standard units of measurement, making it more difficult to realize the way that changes match up across the different signals. This can quickly become confusing to new users since some variables will indicate success by decreasing while others will indicate success by increasing.

SUMMARY

In accordance with one aspect of the present disclosure, there is provided a method including monitoring a signal from each of at least one physiological parameter of an individual to record a set of values for each signal monitored; determining a magnitude of the change of the set of values over time for each signal monitored; identifying each signal exhibiting a magnitude of change in a pre-identified direction and each signal exhibiting a magnitude of change opposite the pre-identified direction; dynamically weighting at least one monitored signal based upon the direction of change of the set of values relative to the pre-identified direction; displaying the monitored physiological signals as an aggregate accentuating the signal values exhibiting a change in the pre-identified direction, wherein each signal is aligned in the same direction; and causing a desired change in at least one monitored signal based upon feedback of the displayed aggregate signals.

In accordance with another aspect of the present disclosure, there is provided a method including monitoring a signal from at least one function to record a set of values for each signal monitored; determining for each signal monitored the relative value of the signal being monitored over time; identifying each signal exhibiting a relative value representing a change in a pre-identified direction and each signal exhibiting a relative value not representing a change in the pre-identified direction, wherein each signal is aligned in the same direction relative to the pre-identified direction; dynamically weighting at least one monitored signal based upon the direction of change of the set of values relative to the pre-identified; displaying the monitored signals as an aggregate accentuating the signal values exhibiting a change in the pre-identified direction; and causing a desired change in at least one monitored function based upon feedback of the displayed aggregate signals.

In accordance with another aspect of the present disclosure, there is provided a system including at least one sensor which monitors a dynamic signal from a function and records a set of values for each signal monitored; a processing device having a memory, the processing device coupled to each of the at least one sensor and configured to execute programmed instructions stored in the memory including obtaining the readings recorded for the set of values from each of the at least one sensor, determining for each signal monitored the relative value of the signal being monitored over time; identifying each signal exhibiting a relative value representing a change in a pre-identified direction and each signal exhibiting a relative value not representing a change in the pre-identified direction, wherein each signal is aligned in the same direction relative to the pre-identified direction; dynamically weighting at least one monitored signal based upon the direction of change of the set of values relative to the pre-identified direction; and a display which shows the monitored signals as an aggregate accentuating the signal values exhibiting a change in the pre-identified direction, such that a desired change is capable in at least one monitored function based upon feedback of the displayed aggregate signals.

In accordance with another aspect of the present disclosure, there is provided a system including at least one sensor which monitors from an individual a dynamic signal from a physiological parameter and records a set of values for each physiological parameter monitored; a processing device having a memory, the processing device coupled to each of the at least one sensor and configured to execute programmed instructions stored in the memory including obtaining the readings recorded for the set of values from each of the at least one sensor, determining the magnitude of the change of the values over time for each signal monitored, identifying each signal exhibiting a magnitude of change in a pre-identified direction and each signal exhibiting a magnitude of change opposite the pre-identified, and dynamically weighting at least one signal monitored based upon the direction of change of the set of values relative to the pre-identified direction; and a display which shows the monitored physiological signals as an aggregate accentuating the signal values exhibiting a change in the pre-identified direction, wherein each signal is aligned in the same direction.

These and other aspects of the present disclosure will become apparent upon a review of the following detailed description and the claims appended thereto.

BRIEF DESCRIPTION OF THE DRAWINGS

The present invention will be more fully understood and appreciated by reading the following Detailed Description in conjunction with the accompanying drawings, in which.

DETAILED DESCRIPTION

Figure 1:
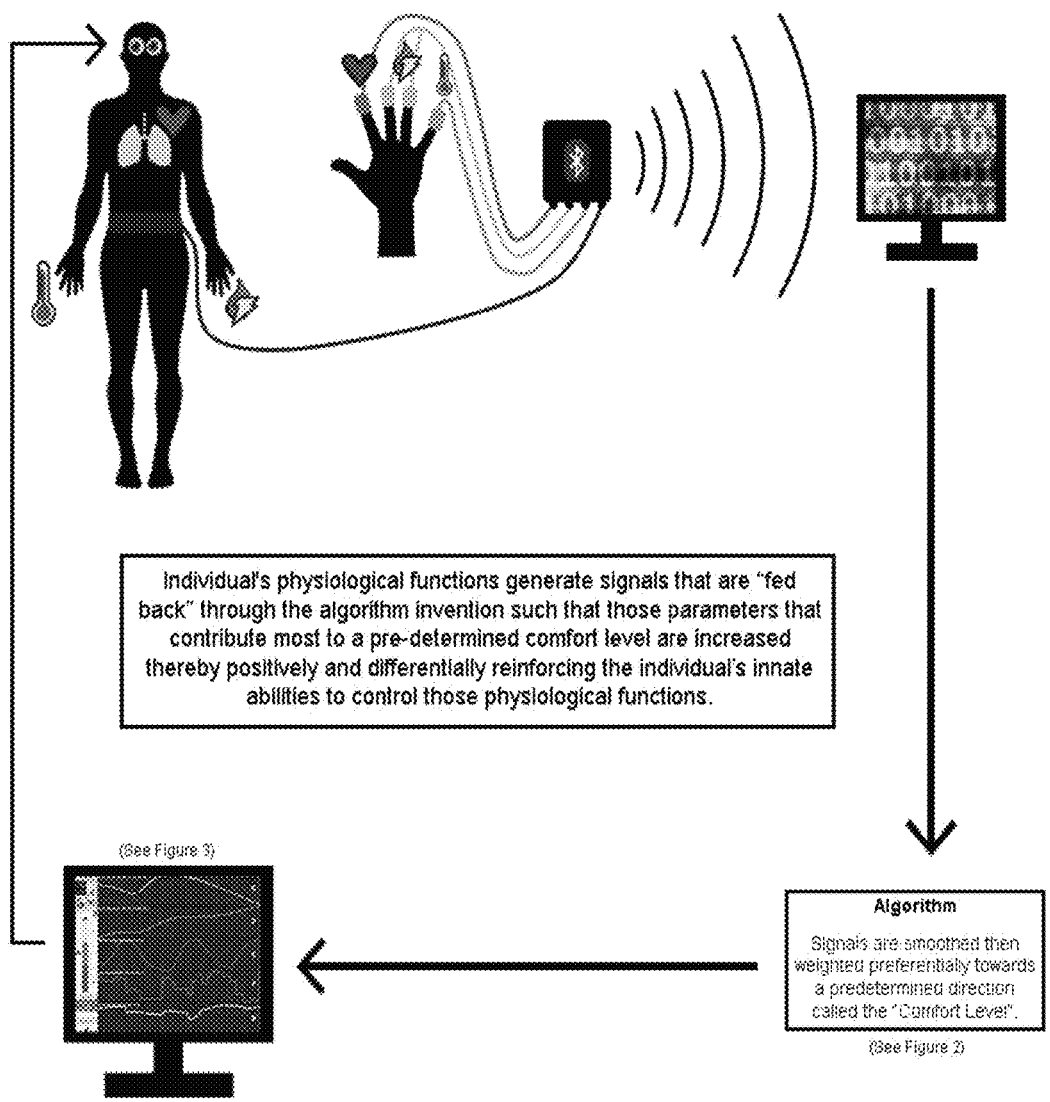
FIG. 1 is a diagram illustrating the information flow from an individual, through the sensors, to the algorithm, and back to the individual who generated the signals according to an embodiment of the invention.

This disclosure relates to the field of feedback control. In accordance with the present disclosure a sensor detects a dynamic function and provides a signal related to the function parameter. The signal is generated by monitoring instrumentation in real-time. The signal is dynamic and can be converted into a stream of values corresponding to the change in function over time. A single or plurality of functions can be monitored to record a set of values for each signal monitored. Multiple sensors and associated monitoring instruments can be arranged in separate channels wherein each signal represents a specific function. Signals are dynamically weighted and displayed showing the monitored signals as an aggregate accentuating the signal values exhibiting a change in a pre-identified direction. The displayed signals include a feedback loop useful for influencing the signals generated.

In an embodiment, the function is a bio function, such as a physiological parameter from an individual. The embodiment relates to psychophysiology with specific application to biofeedback—that is, presenting visual information to users regarding their psychophysiological signals. Biofeedback is typically done by determining the value of a specific signal and displaying a graphical representation of the current value, or value over time, in the standard units of that specific signal. The system and method account for physiological variation by displaying a set of signals and allowing specific signals to take a larger focus if a user is unable to control the others.

A variety of physiological parameters can be monitored with suitable sensors known in the art. Suitable parameters which can be monitored in accordance with the present disclosure include, but are not limited to, skin conductance level ("SCL"), skin temperature ("TMP"), low frequency heart rate variability ("HRV"), respiration rate ("RR"). Other physiological parameters can include groups of electroencephalograhic signals (EEG), quantitative EEG (QEEG), muscles tension as electromyographic signals (EMG), and end-tidal carbon-dioxide concentration (capnograph).

Suitable sensors can include noncontact detectors (e.g. video-based) and contact electrodes, temperature thermistor, skin conductance electrodes, EMG, EEG, photoplethysmograph, capnometer, and other sensors known in the art.

In accordance with an embodiment of the disclosure, a method includes monitoring at least one physiological parameter from an individual to record a set of values for each signal monitored. The direction of the change for each set of values is determined. The signals are aligned to be moving towards a desired goal. The magnitude of signal change can be dynamically weighted based upon the direction of the change of the values. The signals can be displayed in the aggregate showing enhancement of the signals exhibiting a change in a pre-identified direction, e.g. moving towards a desired goal. A signal is dynamically weighted such that when displayed in the aggregate, the signal values exhibiting a change in a pre-identified direction are accentuated. This can be done in various manners. In an embodiment, when displayed the value of each signal exhibiting a change in a pre-identified direction can be enhanced, remain the same or minimized in relation to the other signals. In an embodiment, when displayed, the value of each signal exhibiting a change opposite the pre-identified direction can be enhanced, remain the same or minimized in relation to the other signals. Variations of the above are also possible. In another embodiment, the monitored physiological signals are displayed as an aggregate including the enhanced and non-enhanced values, wherein each signal is aligned in the same direction toward the desired goal. In the aggregate, the signals are referred to as a Dynamic Feedback Signal Set (DyFSS). A feature of the present invention is to dynamically weight and display the monitored signals in a fashion that enhances those signals that are moving in a desired direction.

In an embodiment, monitoring the signal includes tracking the maximum and minimum value of each signal across a specified timeframe. Identifying the value of each signal exhibiting a change in a pre-identified direction includes determining the relative value of a signal by comparing a current value of the signal to the maximum and minimum values. For each signal, the current value is compared to the maximum and minimum within a specified timeframe to calculate relative value. Initially, a signal is monitored over a time sufficient to establish a baseline relative to the maximum and minimum values generated by that signal over the timeframe monitored. For a given function, taking into consideration sensor sensitivity, the nature of the function, and the extent to which the function can change, a person of ordinary skill in the art can determine whether there is sufficient spread between the generated maximum and minimum values to measure fluctuations in the actual value above the normal parameters of noise. If there is insufficient spread between the maximum and minimum, pre-determined values above and below the current value can be used to set the maximum and minimum. The magnitude of the change of the values over time for each set of recorded values is determined in relation to the minimum and maximum values. In an embodiment, the actual value is calculated as a percent of the difference between the minimum and maximum values.

The movement of each signal is displayed such that movement towards a pre-identified direction is movement in the same direction for all signals. For each variable, it is determined whether the current relative value is moving toward or holding steadily in the direction of a desired goal or value. The pre-identified direction can be an increase in magnitude of the signal or a decrease in magnitude of the signal. The pre-identified direction is a movement to or achieving a desired state or goal of a function, such as higher or lower respiration rate, skin temperature, and the like. All values are aligned in a way so that increases and decreases are indicating the same thing and moving in the same direction towards the desired goal, therefore allowing multiple values to be added together in a cohesive manner. For example, if a parameter such as SCL in moving physiologically towards a desired goal tends to exhibit a decreasing value relative to other parameters moving towards a desired goal, then the inverse of value of SCL is used such that all parameters moving towards the desired goal trend in the same direction.

The magnitude of each of the identified set of values exhibiting a change in the pre-identified direction is dynamically weighted to enhance the displayed magnitude of that function. In an embodiment, weighting is calculated so that large values become larger, provided there are other values of functions that are not exhibiting change in the pre-identified direction. Values can be enhanced by a portion of the unused potential contribution amount from the values not exhibiting change in the pre-identified direction being transferred to the values of functions exhibiting change in the pre-identified direction. Conversely, values can be enhanced by a portion of the unused potential contribution amount from the values exhibiting change in the pre-identified direction being subtracted from the values of functions not exhibiting change in the pre-identified direction.

The monitored physiological signals are displayed as an aggregate including the enhanced relative values of functions exhibiting a change in the pre-identified direction and the relative values of functions not exhibiting a change in the pre-identified direction. The displaying can include displaying the set of values as a single visualization. The relative value or enhanced relative value of a signal is translated into a single value that indicates relative comfort. In an embodiment, the displayed values include presenting each monitored signal as a section on a stacked bar. The display of four comfort values can be a combined visual representation, e.g., a stacked bar with each signal's contribution distinguishable as a unique color within the bar, or the sum of the multiple signals displayed as a solid color.

The identifying and dynamically weighting are performed by an algorithm in accordance with the present invention. In an embodiment, the algorithm includes the following: The relative comfort level includes the enhanced value of each signal that is moving towards the desired goal and the relative value of each signal not moving towards the desired goal. The enhanced value of a signal includes an increase by a fraction of the amount that every other signal fails to contribute the maximum it can to the total. Thus, signals that are already making a large contribution are further increased in proportion to the amount that other signals are failing to contribute their maximum to the total. To initiate the algorithm, a baseline recording of each signal is performed to obtain initial minimum and maximum values. A suitable timeframe is 30 seconds, however a longer or shorter timeframe can be suitable. After the baseline recording is completed, the current value of each signal is compared with the minimum and maximum values, wherein the spread between the minimum and maximum values represents 100%, for that particular signal to determine a relative value for that signal. In an embodiment, this is accomplished using the following equation: Weight=(currentVal−minVal/maxVal−minVal). For SCL, the calculation is inverted by adding "1−" to the front of the equation, so that SCL is increasing instead of decreasing so it is aligned with the other signals moving towards the desired goal. Once all the data's relative values are determined, they are summed to provide the relative comfort level. Next, the values are dynamically weighted to ensure that each signal moving towards the desired goal is increased by a fraction of the amount that every other signal fails to contribute the maximum it can to the total. When more than one signal is to be enhanced, the signals can be enhanced by the same or different amounts. Therefore, contributing signals having a larger relative value can receive a bonus weight, which is determined by summing a fraction of the unused portion of each signals potential (DyFSS) value. In an embodiment, this is accomplished using the following equation: Weight=Weight+(misPerc−((1−Weight)/numStrong));
where misPerc refers to the fraction of the total DyFSS value that is unused; (1−Weight) refers to the fraction of the unused portion of that signal's potential maximum DyFSS value; and, numStrong refers to the number of values contributing at least 50% out of their potential 100% to the DyFSS total. Hence, the unused portion of the current signal being calculated is removed from the total unused portion of the combined signals. This remaining portion is compared to the number of signals strongly contributing. The number given by this comparison is the bonus weight, which gets added back to the original relative value. Once all the weights are determined in this manner, they are summed up in order to produce the enhanced relative comfort level.

In an embodiment, an algorithm for comfort level includes:
Weighting

Skin Conductance Weight=1−(currentValue−(minValue/maxValue)−minValue)

Skin Temperature Weight=(currentValue−(minValue/maxValue)−minValue)

Heart Rate Variance Weight=(currentValue−(minValue/maxValue)−minValue)

Respiratory Rate Weight=(currentValue−(minValue/maxValue)−minValue)

Min/Max values update with every new data point or every 60 seconds

Comfort Level=Skin Conductance Weight+Skin Temperature Weight+Heart Rate Variance Weight+Respiratory Rate Weight Comfort Data Point=(comfort DataPoint*9/10)+(comfort Level/10)

Percentages for Bar Graph

Skin Conductance Weight=(1+((misPerc−(1−Skin Conductance Weight))/8))*Skin Conductance Weight Skin Temperature Weight=(1+((misPerc−(1−Skin Temperature Weight))/8))*Skin Temperature Weight Heart Rate Variance Weight=(1+((misPerc−(1−Heart Rate Variance Weight))/8))*Heart Rate Variance Weight Respiratory Rate Weight=(1+((misPerc−(1−Respiratory Rate Weight))/8))*Respiratory Rate Weight misPerc=4−comfort Level Comfort Level=Skin Conductance Weight+Skin Temperature Weight+Heart Rate Variance Weight+Respiratory Rate Weight.

In an embodiment, the method further includes educating the individual that they understand that they are generating the signals and the related goals; and exposing the individual to the display for a sufficient time to establish biofeedback. When viewing the display described above for the purpose of biofeedback training, an individual is provided—fed back—information on his or her own physiological parameters in such a way that the signals that are moving towards a desired goal are emphasized. This positive reinforcement works as a positive feedback loop, conditioning increased ability to control these physiological processes in the desired direction. The parameters—representing physiological functions—that the individual most naturally, already knows how to move in the desired direction are reinforced by being preferentially weighted by the algorithm. Those parameters representing physiological functions that the individual finds more difficult or is unable to change, are de-emphasized by the enhanced comfort level. For example if an individual has impaired sweat gland activity due to a skin condition or medication effect, and his or her SCL changes sluggishly or very little, then the SCL contribution to the total of the values in the DyFSS will appear to be minimized in relation to the enhanced signals. If this individual is adept at adjusting his or her RR and HRV in the desired direction, then that ability will be reinforced by the display of these enhanced signals. As such, the DyFSS differentially reinforces the innate and often diverse abilities of each individual user.

In an embodiment, the method further includes using the signal display for autonomic biofeedback.

This invention applies to a group of parameters that may reflect different aspects of or different ways of measuring one larger concept or function. The multiple parameters may operate on different scales, or fluctuate in opposition to one another, thus the need to transform onto a similar scale and/or invert the value so that movement in a desired direction is always reflected by increasing values. Other embodiments may apply to using the signal display, for example, for monitoring multiple indicators of climate status, multiple flows of financial data, or functioning of various parts of a mechanical device In accordance with an embodiment, a system includes at least one sensor which monitors a dynamic function, such as for example a physiological parameter from an individual, and records a set of values for each signal monitored; a processing device having a memory, the processing device coupled to the at least one sensor and configured to execute programmed instructions stored in the memory including obtaining the readings recorded for the set of values from the at least one sensor, determining the direction of the change for each set of values, dynamically weighting the magnitude of change for each signal based upon the direction of the change including enhancing the value of each signal exhibiting a change in a pre-identified direction and not enhancing the value of each signal exhibiting a change opposite the pre-identified direction; and a display which shows the monitored signals as an aggregate of the enhanced and relative values such that feedback enables influencing monitored signals.

In accordance with an embodiment, a method of translating a user's psychophysiological input into a simplified, meaningful representation of comfort/stress includes receiving multiple signals of the user's psychophysiological state, calculating the necessary psychophysiological variables from the raw data using known methods (e.g., from raw blood volume pulse data, calculating heart rate and then heart rate variability and extracting a specific operating range therein), tracking the range (maximum and minimum) of the variables across a specified time frame, determining the relative value for each signal given the range and current level as it relates to a predetermined direction of change (increase/decrease) or a specific value, dynamically weighting the signals expressing the desired change and displaying the combined, relative and weighted values in a way that indicates the user's enhanced relative comfort level.

In a preferred implementation, the physiological signals relate to functioning of the autonomic nervous system, indicating increases or decreases in either parasympathetic or sympathetic nervous system activation. In an embodiment, a trailing time frame of about one minute can be used to capture the maximum and minimum. In a preferred implementation, the multiple values calculated from the current, relative positions of each signal's value are combined for display as a single bar where the total height indicates the overall comfort level. The bar can either be displayed as a single color, or with separate colors indicating the values of each individual signal. Each aspect is further explained in the following paragraphs.

In an embodiment, the algorithm generalizes a user's comfort level from multiple psychophysiological inputs by using existing hardware and software to collect the input. The four specific signals come from sensors measuring Blood Volume Pulse (BVP), Tidal Volume of Respiration (TVR), peripheral skin Temperature (TMP), and Skin Conductance Level (SCL). Two of these signals are translated further before the calculations are applied: Heart Rate Variability in the low frequency range (HRV, 0.04-0.15 Hz) is calculated from Heart Rate (HR) which is calculated from BVP, while Respiration Rate (RR) is calculated from TVR. Therefore, the four signals that a user sees relate to HRV, RR, TMP, and SCL.

Signals are further transformed before being displayed to the user. A first transformation aligns each signal's change with progress or closeness to a desired outcome state. In this transformation, higher numbers indicate increased comfort or decreased sympathetic arousal. Two of these signals, HRV & TMP, tend to increase with comfort already and are not transformed. One signal, SCL, is inversely related: a measured decrease of the signal is transformed to an increase and vice-versa. The final signal, RR, relates both directly and inversely depending on the range; when the value measured is between zero and six breaths per minute, it enters the next translation directly while it is inverted when measured at values above six breaths per minute.

With each signal's value increasing directly with increased comfort, the calculations determine the relative comfort value as will be presented to a user. A maximum and minimum value for each signal is tracked across a specified time frame. In the event that an insufficient difference exists between the measured maximum and minimum to determine fluctuations above normal parameters of noise, a predetermined spread is applied to the signal to establish the maximum and minimum. The spread between maximum and minimum, whether measured or set internally, is the window of measurement to which a signal's current value is compared. Where the current value lies within that window is the relative comfort contribution from that signal.

For example, an implementation can include the relative comfort value from four signals ranging from 0 to 2.5. These four values can be summed to provide a total ranging from 0 to 10. A signal's relative comfort value of 0 means that the signal's current value is the current minimum within the trailing time frame, thereby making no contribution to total comfort. A signal's relative comfort value of 2.5 means that the signal's current value is the current maximum, thereby making a large contribution to total comfort.

A weighting-scheme further increases or decreases the relative comfort contribution from specific signals based on performance. Without weight-adjusted values, each signal could contribute a maximum of 2.5, out of the total 10, toward total comfort. However, it is likely that there will be variation among the signals with some remaining near 0 and others near 2.5. Weighting increases the values for signals that are higher to emphasize the signals that are making a large contribution to overall comfort while similarly de-emphasizing the values for signals that are making little or no contribution to overall comfort. It is possible, then, that one signal contributes more than 2.5 to total comfort. It is not possible for a signal to contribute less than 0.

The final values determined by the calculations can be presented to users in a way similar to existing displays. Physiological values are commonly displayed individually as colorful bars that indicate the current level. Different signals are typically displayed in different units, and therefore are presented separately. From the algorithm presented above, the different signals are transformed into comparable units, allowing the multiple signals to be more easily combined into a single measure. The values from this algorithm for example can be displayed as a single, stacked bar graph ranging from 0 to 10. Each signal's contribution is displayed as a separate color so that users can see the individual contributions. An alternate display method is also possible by which the entire bar is the same color. This alternate display method shows overall comfort without identifying the contribution of each individual signal. Additional visualization options are possible.

The present method of calculating and displaying physiological readings can be used by clinicians in therapeutic encounters with clients or by individuals who are interested in visualizing or tracking their wellbeing on their own. The process of simplifying multiple physiological signals also allows easier integration of biofeedback into therapeutic video games that can be played clinically or recreationally.

A clinician whose patients exhibit high levels of anxiety can employ biofeedback training. This method is useful in teaching patients to self-regulate their own body's responses. The clinician attaches sensors to the hands and around the waist of the patient while describing the specific physiological signals that are recorded. During the course of training, the patient learns behaviors that increase and decrease comfort as measured by the signals. The skills of controlling the body's comfort level can then be applied to events and situations that may occur in the patient's daily routines.

This algorithm could be embedded into other media or devices to which sensors can be added such as interactive games as a controller and mechanical devices (e.g., motor vehicles, airplane seats) allowing the user's physiological input to affect game mechanics or give feedback on autonomic balance while engaged in using the mechanical device.

The mathematical translation makes the signals readily comparable and able to be combined (i.e., increases/decreases are interpreted similarly) and/or compared (e.g., each measured number can only range from 0-2.5) in a meaningful way. An important first step in allowing the combined display to work as a whole.

One advantage of a combined display, opposed to viewing signals as disconnected pieces, is that it decreases the attentional demand on users. Users, and clinicians/teachers aiding in the learning process, do not need to look all over the screen and decide which signal to focus on. Within this combined display, the algorithm automatically emphasizes which signals are moving or holding a steady value in the desired direction, further decreasing the mental load to interpret changes.

The combined display also simplifies interpretation by having all signals move in the same direction. That is, bigger numbers are associated with success at moving toward comfort. A user who is able to gain further sophistication and learn about the various signals can go on to develop an understanding of the physiological signals, their standard units, and the meaning of increases/decreases therein.

While biofeedback training is widely used it is not a large area of research. The present system and method can be applied to actively studying and disseminating research on autonomic biofeedback in young people with autism spectrum disorder. Most who use biofeedback do not attempt to alter commercially available algorithms and displays because they do not recognize the challenge of working therapeutically with neurologically diverse population. Much more effort is being put into remote sensing of physiological signals with wearable devices than how well the signals are transformed to help the user develop self-control.

The DyFSS could be commercialized as part of a larger package of biofeedback software as the underlying method that contributes to multiple different display options. It also lends itself to integration with other interactive games and media as an aspect of control.

When the DyFSS is used for peripheral autonomic biofeedback for example, each sensor and its purpose are explained to the individual user. After the sensors are placed on the individual, he or she is shown how he or she can control the signal generated by each sensor. For example, when the individual is asked to hold his or her breath, warm his or her hands, or act tense, he or she can note that a graphical display changes in a predictable manner and direction in response to that behavior. The individual is also informed of the desired direction of the parameters derived from the signals in order to achieve a given physiological objective, for example decreased comfort ("fight or flight," sympathetic nervous system arousal) and increased comfort (parasympathetic or vagal tone).

EXAMPLES

Figure 2A:
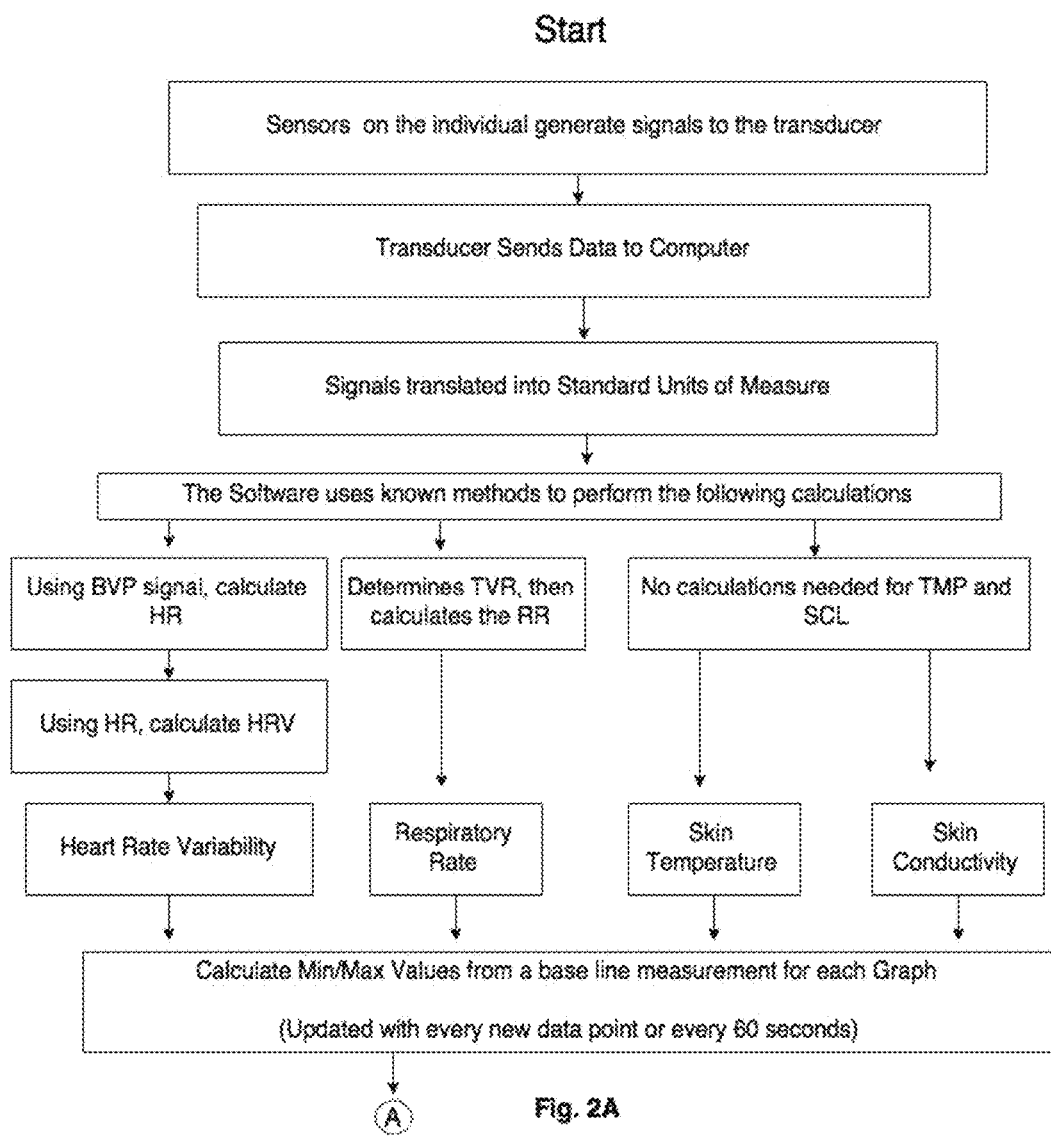
FIGS. 2A, 2B, and 2C each illustrate portions of a flow chart showing signal modification of comfort level signals according to an embodiment of the invention.
Figure 2B:
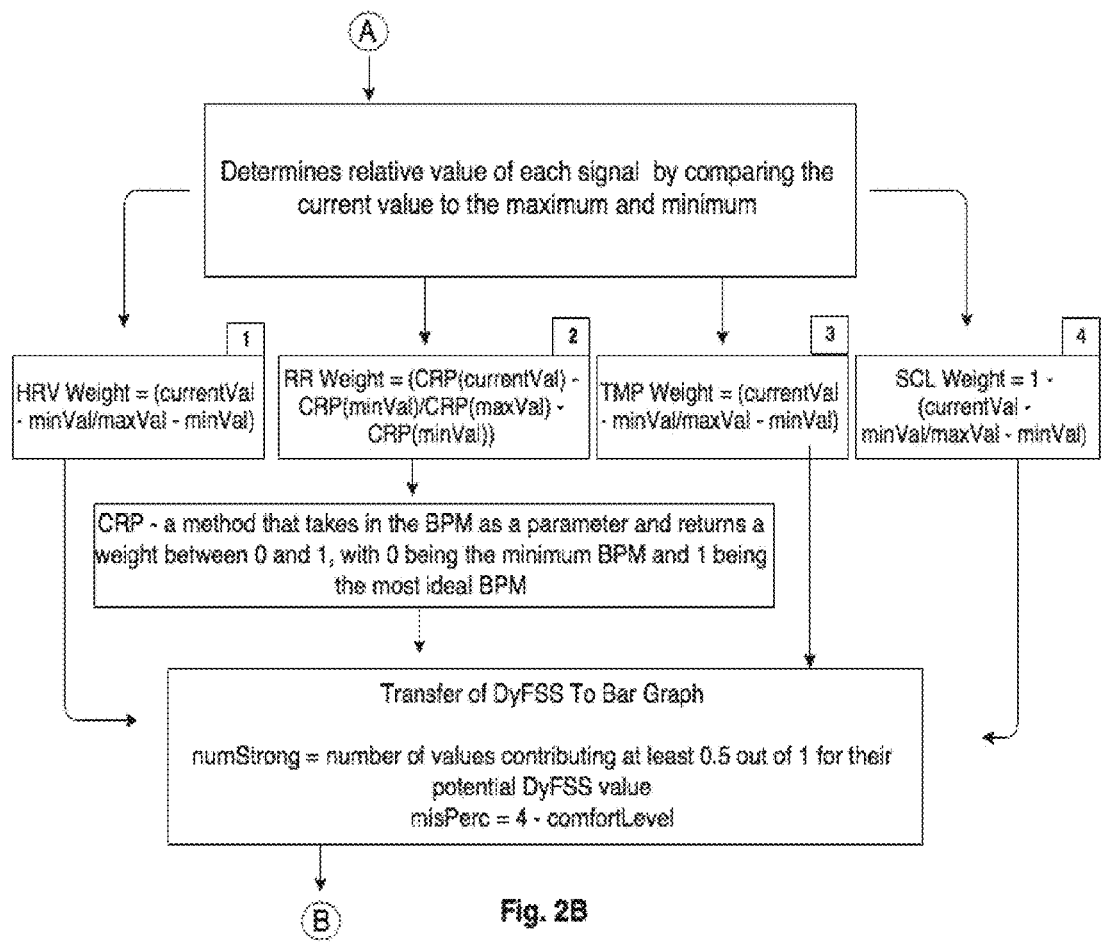
Figure 2C:
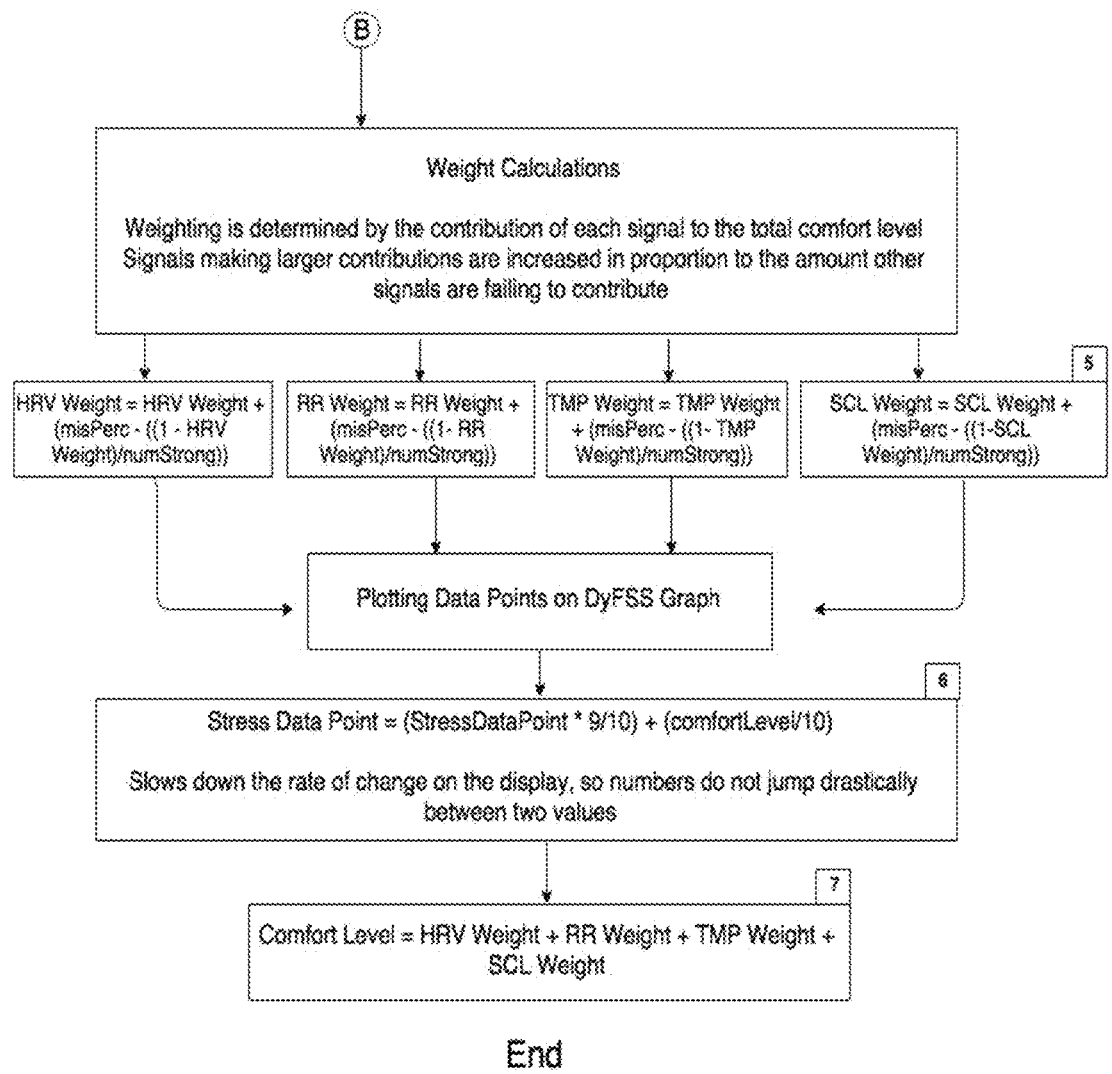

In this example, information flow from individual, through the sensors, then the algorithm, and back to the individual who generated the signals in order to feed back reinforcement of physiological control is shown in FIG. 1. Signals are captured through individual sensors. For respiration rate, a stretch-sensitive belt measures abdominal girth as the user breathes in and out, and these values are used to determine respiration rate. Commonly respiratory rates vary in adolescents and adults form 12-18 breaths per minute (BPM). To maximize comfort and vagal tone, a respiratory rate in the 6-8 BPM is desired. For skin conductance level, a direct function of sympathetic arousal, two electrodes measure the sweat gland activity from the middle and ring fingertips. Baseline skin conductance varies in normal individuals from 1 to 10 microSiemens (µs) and is also affected by environmental conditions such as ambient temperature and humidity. For the purposes of biofeedback training, however the decrease of 40-60% in skin conductance from a given baseline is desired. So a decrease in skin conductance over a training session from 10 to 4 µs can be as significant as a decrease from 4 to 1 µs. For skin temperature, a thermister also collects the values from the fifth fingertip that can be converted into degrees Fahrenheit or Celsius. Peripheral skin temperature is a proxy for peripheral blood flow, which increases with increasing vagal tone and generally decreases with sympathetic arousal. Peripheral skin temperatures are also affected by ambient temperature. In general, a skin temperature of 96.5 degrees Fahrenheit indicates increased vagal and decreased sympathetic tone. For heart rate variability, blood volume pulse is collected from the index finger using a photoplethysmograph, and these values are used to determine the inter-beat interval that is, in turn, used to calculate heart rate variability. Heart rate variability frequency that centers around 0.10 Hertz (range 0.04-0.15, or about 4-8 cycles per minute) correlates with physiological state of increased vagal tone. These signals are transferred to the computer through a multi-channel device. Once they arrive at the computer, the signals are transformed, using known methods, into the four values used by the algorithm: RR, SCL, TMP, and HRV. FIG. 2 shows a flowchart of signal modification from signal input to display illustrating demonstrates how signals are modified through the invention including formulae for smoothing and preferential weighting.

Examples using data are provided in FIG. 2 as indicated in the flowchart:

The algorithm compares the current reading to the signal's maximum (5 ms in this example) and signal's minimum (3 μs) to determine the DyFSS value. In this example, the current reading is 4 μs, so with the translated DyFSS value ranging from a possible 0 (no comfort) to a possible Example No.

1)  Current Value: 54           HRV Weight = (54 − 46/67 − 46)
    Minimum Value: 46           HRV Weight = 0.38
    Maximum Value: 67
2)  Current Value: 12 BPM       RR Weight = (CRP(12) − CRP(8)/CRP(15) − CRP
                                (8))
    Minimum Value: 8 BPM        TMP RR Weight = 0.57
    Maximum Value: 15 BPM
3)  Current Value: 75.22        TMP Weight = (75.22 − 75.11/75.33 − 75.11)
    Minimum Value: 75.11        TMP Weight = 0.5
    Maximum Value: 75.33
4)  Current Value: 2.86         SCL Weight = 1 − (2.86 − 2.83/2.9 − 2.83)
    Minimum Value: 2.83         SCL Weight = 1.94
    Maximum Value: 2.9
5)  numStrong = 2(SCL and RR Weight)  SCL Weight = 1.94 + (0.61 − ((1 − 1.94)/2))
    misPerc = 4 − 3.39 = 0.61   SCL Weight = 3.02
    SCL Weight = 1.94
    RR Weight = 0.57
6)  Previous Comfort Data Point = 0.327  Comfort Data Point = (0.327 * 9/10) + (3.39/10)
    Comfort Level = 3.39        Comfort Data Point = 0.63
7)  HRV Weight = 0.38           Comfort Level = 0.38 + 0.57 + 0.5 + 1.94
    RR Weight = 0.57            Comfort Level = 3.39
    TMP Weight = 0.5
    SCL Weight = 1.94

Abbreviations

BVP: Blood Volume Pulse
SCL: Skin Conductance Level
HR: Heart Rate
HRV: Heart Rate Variability measuring the percentage of HRV in the low frequency band (0.04-0.15 Hz)
TMP: Skin Temperature
BPM: Breaths Per Minute
RR: Respiration Rate
TVR: Tidal Volume of Respiration In order to be compiled for the algorithm each signal is processed to maximize its window of measurement and align its direction of change. Considering a discussion of only SCL for example, it has an associated minimum spread within the signal's window of measurement (the distance between the recent maximum and minimum). Minimum spread is set at 0.6 μs. The SCL signal also is reversed before it is used in the algorithm, such that the translated value indicates progress toward the goal state (e.g., a physiological response that indicates greater comfort). This can be done by storing the maximum for the signal as "minimum" and the minimum for the signal as "maximum," and the translated value ranging from 0 (low comfort) to 1 (high comfort) opposite to the increase and decrease of the signal's actual reading. The signal direction is reversed since a high SCL signal typically indicates lower comfort or increased arousal.

The timeframe for tracking the signal's recent minimum and recent maximum, in this example, is one minute. The same amount of time is also used for the length of the baseline recording. During the baseline, the SCL signal fluctuates as high as 5 μs and as low as 3 μs. The 2 μs difference is wider than the minimum spread needed to determine fluctuations above the normal parameters of noise, so the algorithm can use the recorded numbers from the signal rather than create numbers above and below the current reading to be used as maximum and minimum.

1 (high comfort), the SCL's contribution to the total DyFSS number, before further weighting, is 0.5. This represents that the reading is at 50% of its possible maximum relative value. If there had been insufficient spread at the end of the baseline recording time frame, then the minimum and maximum would be set to 3.7 and 4.3 to create a spread of 0.6 surrounding the current signal reading of 4.0, therefore the current reading lands between the maximum and minimum at 50%.

The minimum, maximum, and current reading are continually updated across the most recent one-minute timeframe as the recording continues. For this example, time continues and the SCL signal then decreases to 3 μs and stays there for more than one minute. This means that the actual maximum and minimum signal recording across that minute would both be 3 ms. However, since the minimum spread dictates a 0.6 difference must exist between the maximum and minimum, the current signal reading will remain as reported (3 μs), and the recent minimum will remain as reported (3 μs), but the recent maximum will not go below 3.6 as long as the minimum signal reading does not drop below 3 and the current signal reading does not increase above the calculated maximum (3.6). This is different from determining the value.

Once all of the possible signals are translated into their respective DyFSS values, then weighting of the signals can occur. Weighting is done to emphasize signals that are moving successfully toward the stated goal. In this example, the signals are physiological recordings that indicate increased or steady levels of comfort relative to the most recent one minute. Weighting occurs by dividing a portion the non-contributing space among the strong signals. Non-contributing space is the remaining value from all signals that is not being added to the DyFSS value total. For example, if TMP is contributing 0.7 of its possible 1.0, the non-contributing space is 0.4. Strong signals are ones that, of a possible 1, are contributing at least 0.5 of their value. Each strong signal has the potential to increase its value by the total of the non-contributing space from each other signal. That is, all the non-contributing space except for the individual signal's non-contributing space. Each signal's potential bonus is then divided by the number of strong signals, i.e., the number of signals that receive an increase. The final calculated bonus is directly added to the signal's current relative value. So, if SCL is 0.6 and TMP is 0.7, while RSP is 0.4 and HRV is 0.3, there are two strong signals (SCL and TMP), and the total non-contributing space is 0.4 (from SCL)+0.3 (from TMP)+0.6 (from RSP)+0.7 (from HRV)=2.0. The value for SCL will be increased by the non-contributing space of the other signals (0.3+0.6+0.7=1.6) divided by the number of strong signals (2), for a total increase in its value by 0.8. So, the enhanced value for SCL includes 0.6 from its relative value plus an additional 0.8 from its dynamic weighting to obtain a total DyFSS enhanced value of 1.4. Similarly, the enhanced TMP value includes its relative value of 0.7 plus 0.85 (0.4+0.6+0.7=1.7/2) for dynamic weighting to obtain a total DyFSS enhanced value of 1.55. The DyFSS contribution for RSP is 0.4 and for HRV is 0.3 (their relative values), which are not enhanced. Thus, in this example the bonus value is divided evenly between the strong signals. However, in other examples, the non-contributing space of the other signals can be divided unevenly between the strong signals, as desired.

Figure 3:
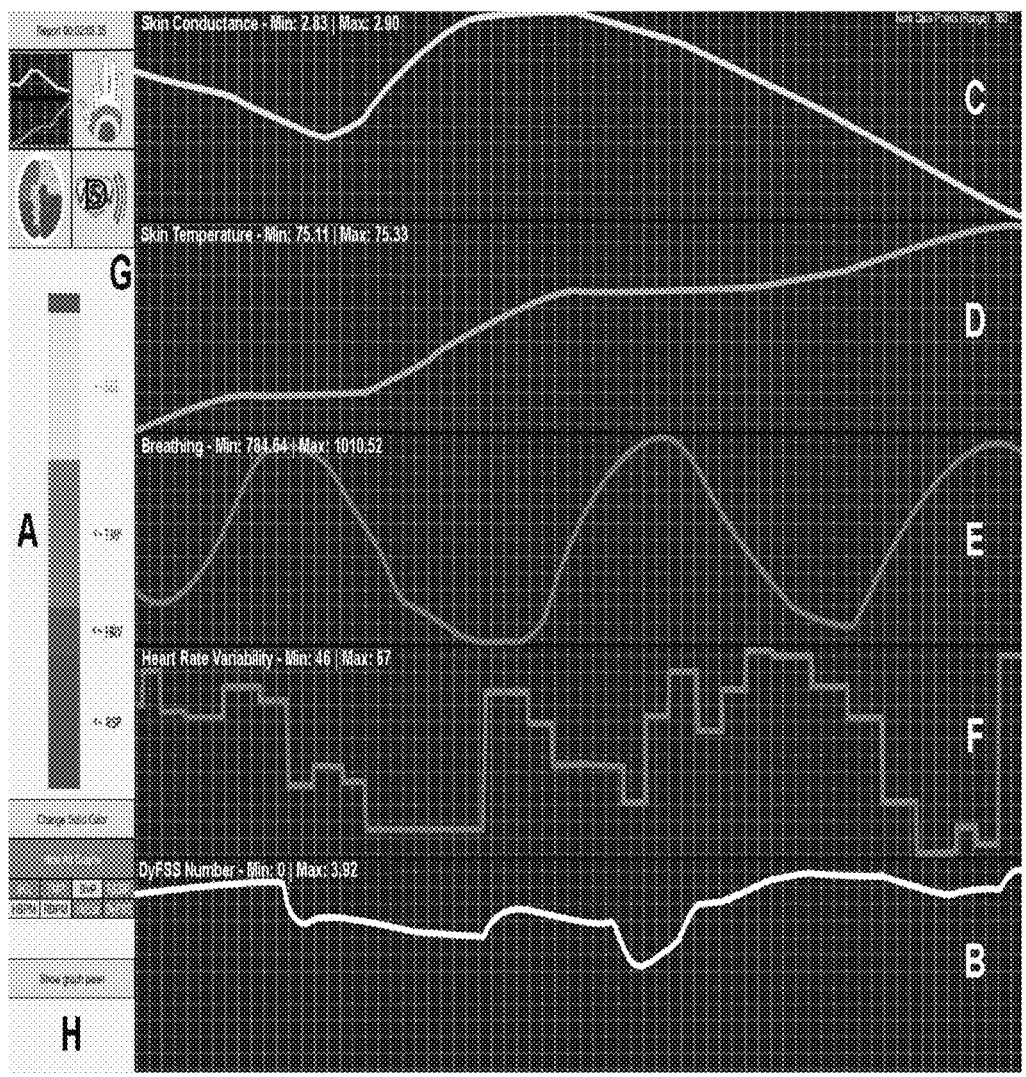
FIG. 3 is an example of the graphical user interface generated in the biofeedback embodiment of FIG. 1 according to an embodiment of the invention.

At the computer, these four values are combined through the algorithm. The algorithm's final value composed of enhanced values and relative values of the monitored signals is displayed in real-time on the computer monitor. Users can see the change in their physiological responses based on their success in moving or holding steady toward the determined "goal states" of each variable. In one implementation, the final values appear as four pieces of a stacked bar graph, where success is associated with an increase in the size of the bar. FIG. 3 illustrates an example of the graphical user interface (display) in the biofeedback embodiment to allow positive and differential reinforcement of physiological function in the user shown in FIG. 1. The following are labels used in FIG. 3 as indicated:

A. DyFSS Bar Graph: The relative value of each signal is translated into a single value which indicates relative comfort. Each individual signals contribution towards the relative comfort is stacked on top of one another to provide a visual representation of the overall comfort level. The bar is displayed either as a solid color, or with each signal having a unique color to show its individual contribution.

B. DyFSS Graph: The Data from all the above graphs undergoes weight calculations and are summed together to determine the DyFSS number and overall comfort level. Data points are determined based upon the previous data point, ensuring that there is a smooth curve between points.

C. Skin Conductance Graph: Data collected from the skin conductance sensors is displayed graphically to represent sweat levels.

D. Skin Temperature Graph: Data collected from the Skin Temperature Sensor is displayed graphically to represent skin temperature.

E. Breathing Graph: Data collected from the strain gauge is displayed graphically to represent respiratory effort.

F. Heart Rate Variability Graph: Data collected from the Blood Volume Pulse sensor is displayed graphically to represent the percentage of low frequency range heart rate variability.

G. Alternate GUI Buttons: These buttons are used to toggle between different displays based upon the user's preference. Options include the graphical display, hand display, brain display, and the stress destroyer game. Above these there is a report screen button, which will stop recording data and allows the user to view the entire session.

H. Graph Display Buttons: These buttons are used to toggle the display of the different graphs, including Skin Conductance, Skin Temperature, Heart Rate Variance, Respiratory Rate, Blood Volume Pulse, Heart Beats Per Minute, Breaths Per Minute and the DyFSS Graph. There is also a button to toggle the graphical display and to switch between a solid color for the comfort level bar graph and multiple colors.

The Minimum and Maximum Values for each graph (not including the bar graph) are displayed in the upper left hand corner, and update with every new data entry or every 60 seconds.

The individual participating in autonomic biofeedback training as described above views this graphic display and receives information on those parameters representing physiological functions that he or she can best control in the desired direction. The preferential weighting of those parameters that the individual most easily controls serves as differential or selective reinforcement of those physiological functions as noted above.

Although various embodiments have been depicted and described in detail herein, it will be apparent to those skilled in the relevant art that various modifications, additions, substitutions, and the like can be made without departing from the spirit of the disclosure and these are therefore considered to be within the scope of the disclosure.

What is claimed:

1. A method comprising:
   monitoring, by a sensor, a signal from each of at least two functions to record a set of values for each signal monitored;
   determining, by a processing device, for each signal monitored the value of the signal relative to a desired goal being monitored over time;
   identifying, by a processing device, each monitored signal exhibiting a relative value representing a change in a pre-identified direction and each monitored signal exhibiting a relative value not representing a change in the pre-identified direction, wherein each identified signal is aligned in the same direction relative to the pre-identified direction;
   dynamically weighting, by a processing device, each of the aligned signals based upon the determined value relative to the desired goal of each of the aligned signals;
   summing, by a processing device, the dynamically weighted signals to a finite total value;
   adjusting, by a processing device, each dynamically weighted signal based upon the performance of each of the aligned signals relative to each other over time while maintaining the finite total value;
   displaying over time the dynamically weighted signals as an aggregate; and
   causing a desired change in at least one monitored function based upon feedback of the displayed aggregate signals.

2. The method of claim 1, wherein determining the relative value of a signal comprises comparing a current value of the signal to the monitored maximum and minimum values of the signal.

3. The method of claim 1, wherein the function comprises a physiological parameter of an individual.

4. The method of claim 1, wherein the dynamically weighting comprises enhancing the relative value of a signal representing a change in a pre-identified direction at or above about 50% of the difference between the minimum and maximum values of the signal.

5. The method of claim 1, wherein the pre-identified direction comprises an increase in magnitude of the signal.

6. The method of claim 1, wherein the pre-identified direction comprises a decrease in magnitude of the signal.

7. The method of claim 1, wherein the displaying comprises displaying the set of values as a single visualization.

8. The method of claim 1, wherein the dynamically weighting is performed by an algorithm comprising the following: Weight=(currentVal−minVal/maxVal−minVal) and Weight=Weight+(misPerc−((1−Weight)/numStrong)); where misPerc refers to the fraction of a total Dynamic Feedback Signal Set value that is unused; (1−Weight) refers to the fraction of the unused portion of that signal's potential maximum Dynamic Feedback Signal Set value; and, numStrong refers to the number of values contributing at least 50% out of their potential 100% to the Dynamic Feedback Signal Set.

9. A system comprising:
 at least one sensor which monitors a dynamic signal from at least two functions and records a set of values for each signal monitored;
 a processing device having a memory, the processing device coupled to each of the at least one sensor and configured to execute programmed instructions stored in the memory comprising obtaining the readings recorded for the set of values from each of the at least one sensor, determining for each signal monitored the value of the signal relative to a desired goal being monitored over time; identifying each monitored signal exhibiting a relative value representing a change in a pre-identified direction and each monitored signal exhibiting a relative value not representing a change in the pre-identified direction, wherein each identified signal is aligned in the same direction relative to the pre-identified direction; dynamically weighting each of the aligned signals based upon the determined value relative to the desired goal of each of the aligned signals; summing the dynamically weighted signals to a finite total value; and adjusting each dynamically weighted signal based upon the performance of each of the aligned signals relative to each other over time while maintaining the finite total value; and
 a display which shows the dynamically weighted signals as an aggregate, such that a desired change is capable in at least one monitored function based upon feedback of the displayed aggregate signals.

10. The system of claim 9, wherein determining the relative value of a signal comprises comparing a current value of the signal to the monitored maximum and minimum values of the signal.

11. The system of claim 9, wherein the function comprises a physiological parameter of an individual.

12. The system of claim 9, wherein the dynamically weighting comprises enhancing the relative value of a signal representing a change in a pre-identified direction at or above about 50% of the difference between the minimum and maximum values of the signal.

13. The system of claim 9, wherein the pre-identified direction comprises an increase in magnitude of the signal.

14. The system of claim 9, wherein the pre-identified direction comprises a decrease in magnitude of the signal.

15. The system of claim 9, wherein the displaying comprises displaying the set of values as a single visualization.

16. The system of claim 9, wherein the dynamically weighting is performed by an algorithm comprising the following: Weight=(currentVal−minVal/maxVal−minVal) and Weight=Weight+(misPerc−((1−Weight)/numStrong)); where misPerc refers to the fraction of a total Dynamic Feedback Signal Set value that is unused; (1−Weight) refers to the fraction of the unused portion of that signal's potential maximum Dynamic Feedback Signal Set value; and, numStrong refers to the number of values contributing at least 50% out of their potential 100% to the Dynamic Feedback Signal Set total.

* * * * *